(12) United States Patent
Kang et al.

(10) Patent No.: US 9,717,411 B2
(45) Date of Patent: Aug. 1, 2017

(54) INTRAOCULAR PRESSURE SENSOR AND METHOD FOR MANUFACTURING SAME

(75) Inventors: Byung Joo Kang, Seoul (KR); Ji Sung Jo, Jeollabuk-do (KR); Chang Kun Park, Gyeonggi-do (KR)

(73) Assignee: SOONGSIL UNIVERSITY RESEARCH CONSORTIUM TECHNO-PARK, Seoul (KR)

( * ) Notice: Subject to any disclaimer, the term of this patent is extended or adjusted under 35 U.S.C. 154(b) by 748 days.

(21) Appl. No.: 14/350,123

(22) PCT Filed: Nov. 24, 2011

(86) PCT No.: PCT/KR2011/009009
§ 371 (c)(1),
(2), (4) Date: Apr. 7, 2014

(87) PCT Pub. No.: WO2013/051755
PCT Pub. Date: Apr. 11, 2013

(65) Prior Publication Data
US 2014/0243646 A1    Aug. 28, 2014

(30) Foreign Application Priority Data

Oct. 7, 2011    (KR) .......................... 10-2011-0102571

(51) Int. Cl.
*A61B 3/16*    (2006.01)
*H01B 13/00*    (2006.01)

(52) U.S. Cl.
CPC ...................................... *A61B 3/16* (2013.01)

(58) Field of Classification Search
None
See application file for complete search history.

(56) References Cited

U.S. PATENT DOCUMENTS

| | | | |
|---|---|---|---|
| 6,517,483 B2* | 2/2003 | Park | A61B 3/16 600/398 |
| 8,025,625 B2* | 9/2011 | Allen | A61B 5/021 600/300 |
| 2006/0177956 A1* | 8/2006 | O'Brien | B81B 7/007 438/50 |
| 2011/0071505 A1 | 3/2011 | Rickard et al. | |

FOREIGN PATENT DOCUMENTS

| | | |
|---|---|---|
| JP | 06-331467 A | 12/1994 |
| KR | 10-0300527 B1 | 10/2001 |
| KR | 10-2003-0079280 A | 10/2003 |
| KR | 10-2004-0051464 A | 6/2004 |
| KR | 10-2011-0054584 A | 5/2011 |

* cited by examiner

*Primary Examiner* — Shamim Ahmed
(74) *Attorney, Agent, or Firm* — Revolution IP, PLLC

(57) ABSTRACT

Disclosed is a method of manufacturing an intraocular pressure sensor that is put into an eyeball of a patient and measures the intraocular pressure, the method comprising: preparing a first substrate; depositing a base film on the bottom of the first substrate; exposing the top of the base film by etching the first substrate; applying epoxy onto the center of the exposed base film; disposing the first electrode at the epoxy-applied portion on the base film; preparing a second substrate; depositing a support film onto the second substrate; forming a second electrode on the support film; exposing the bottom of the support film by etching the second substrate; and disposing the second substrate onto the first substrate.

12 Claims, 11 Drawing Sheets

[FIG. 1]
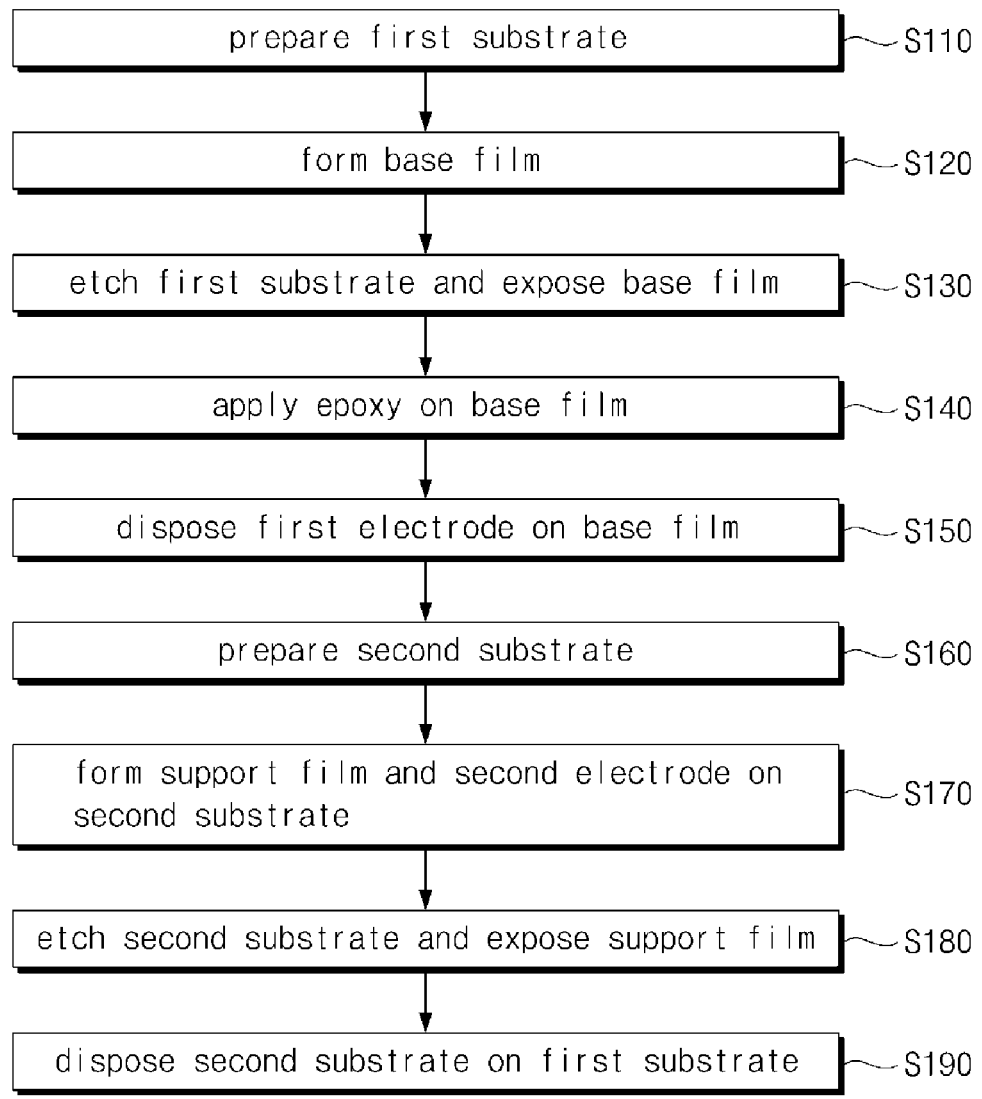

[FIG. 2]
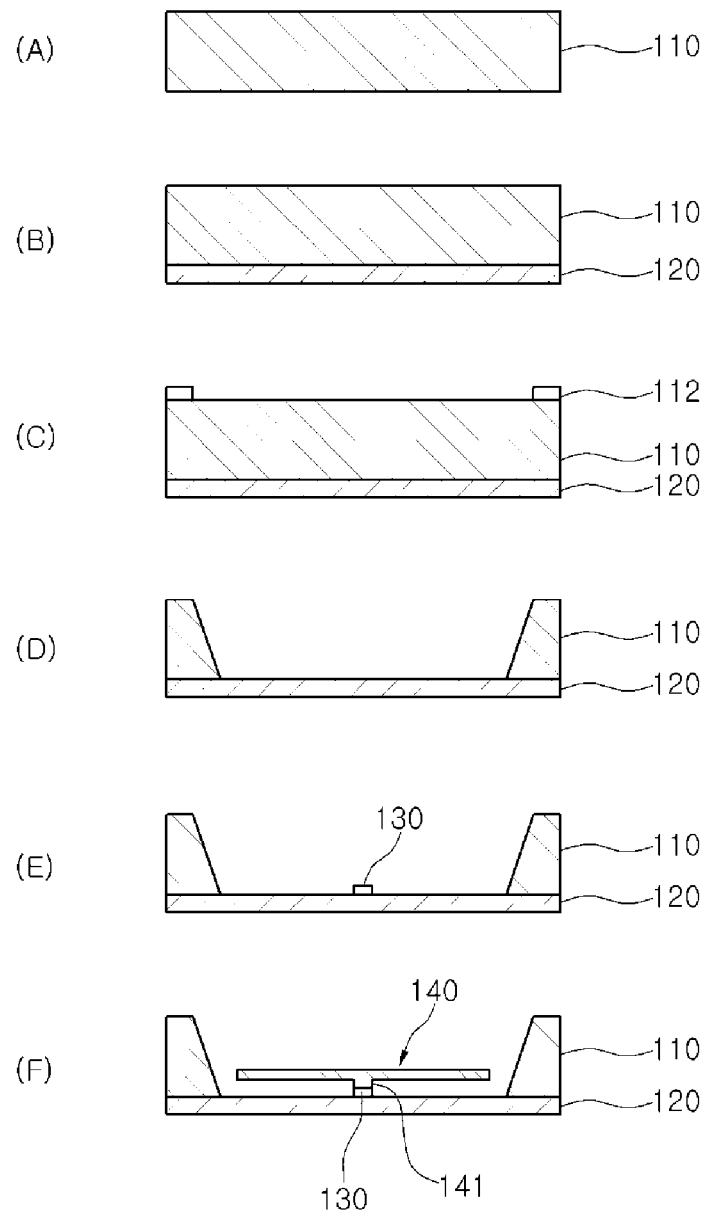

[FIG. 3]
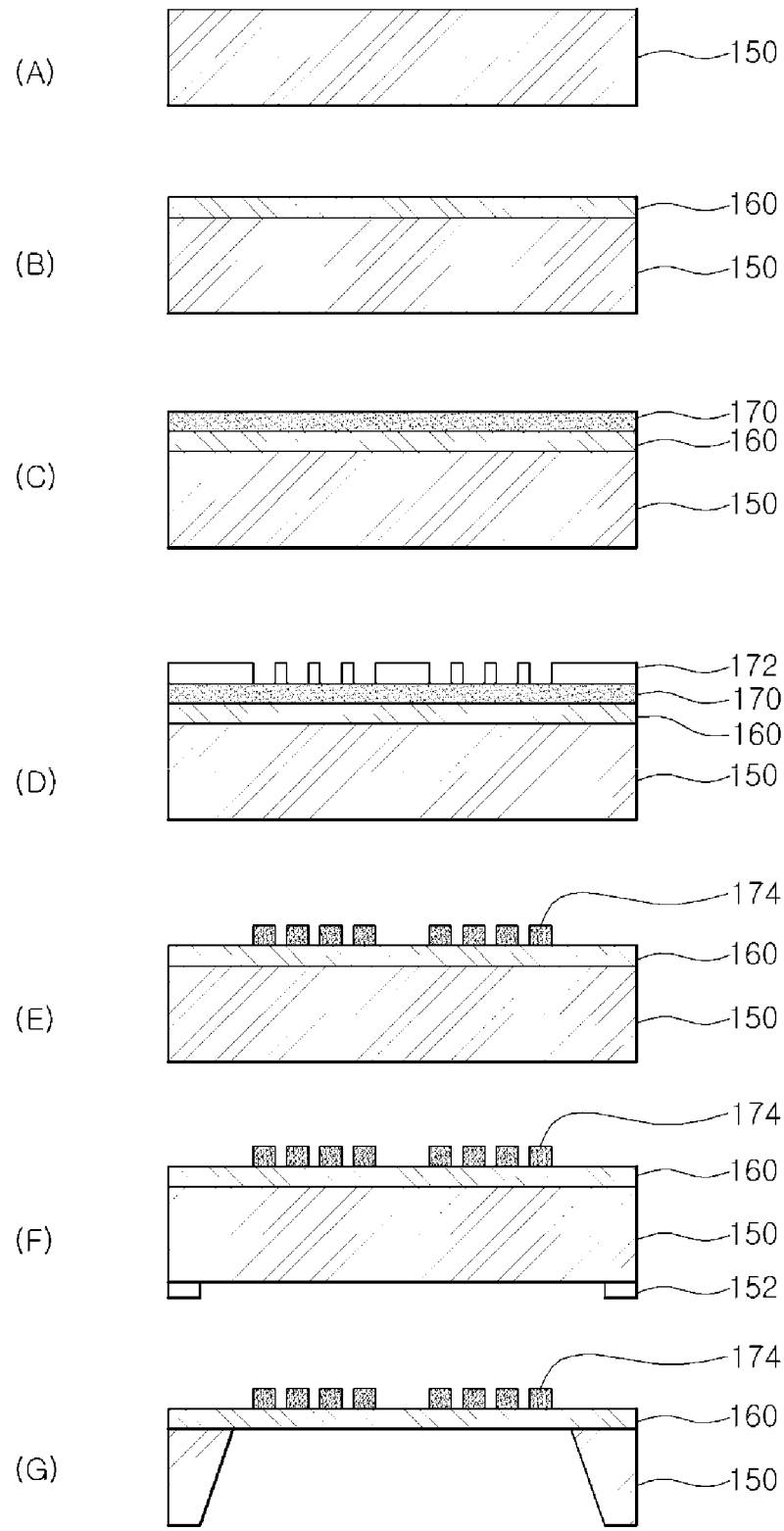

[FIG. 4]
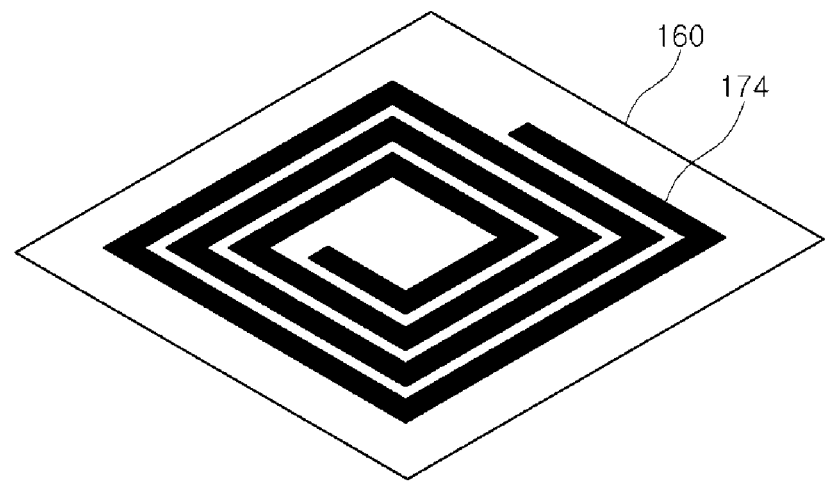
[FIG. 5]
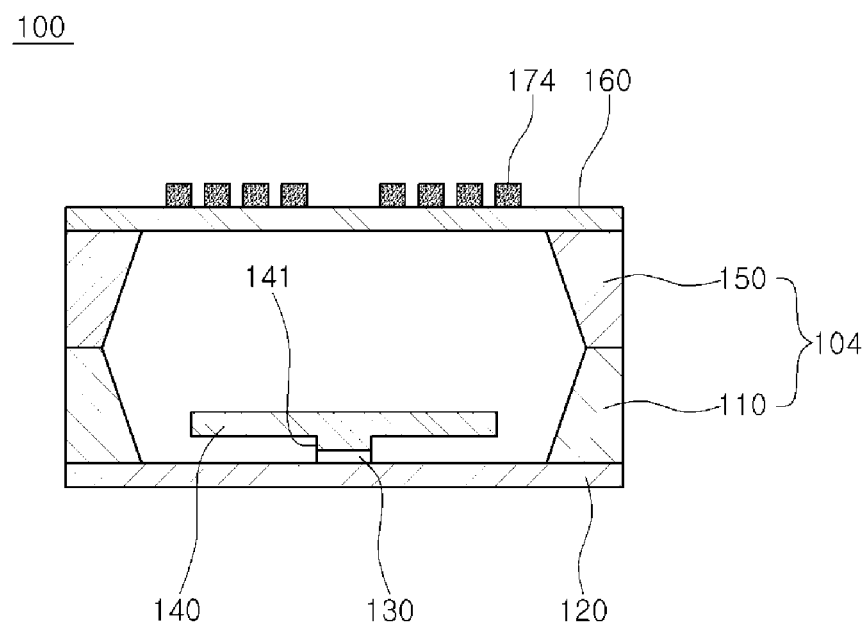

[FIG. 6]
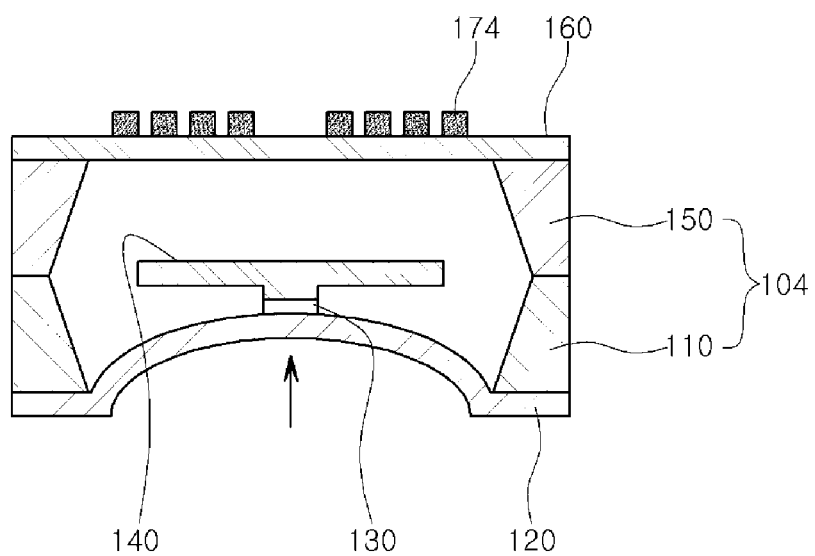

[FIG. 7]
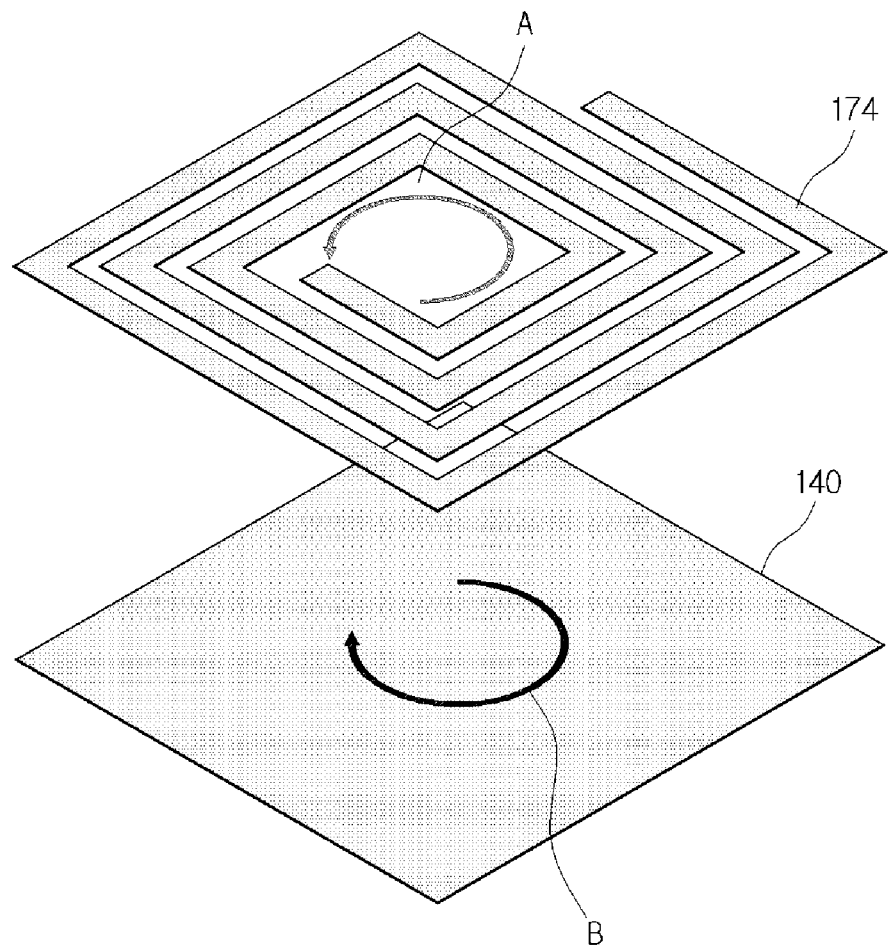
[FIG. 8]
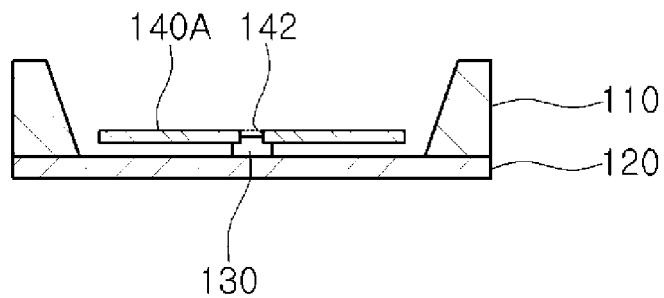

[FIG. 9]
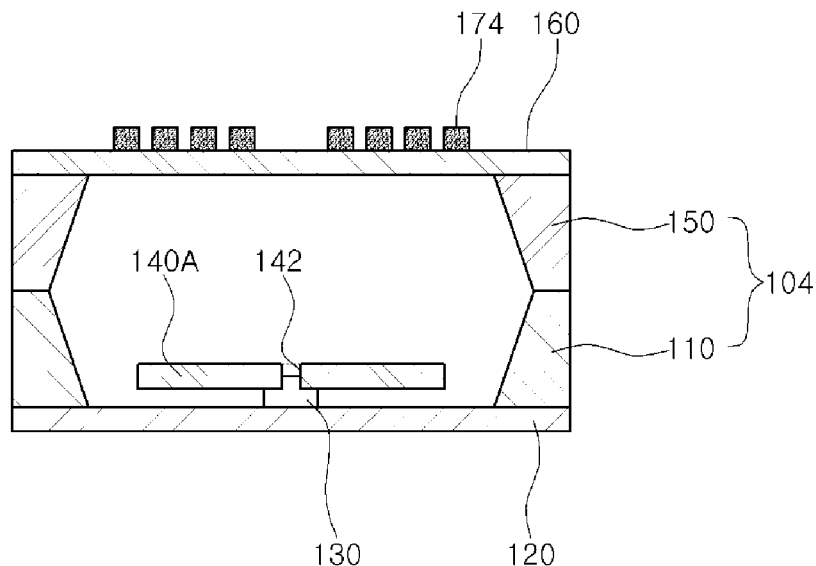
[FIG. 10]
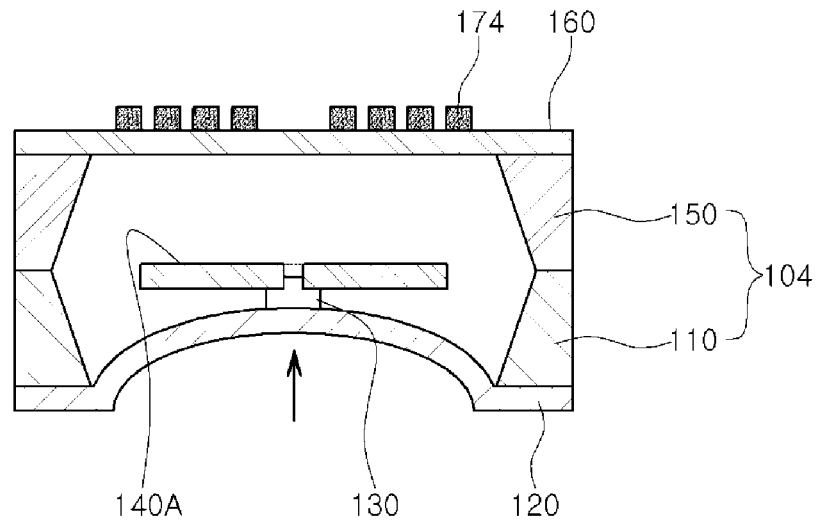

[FIG. 11]
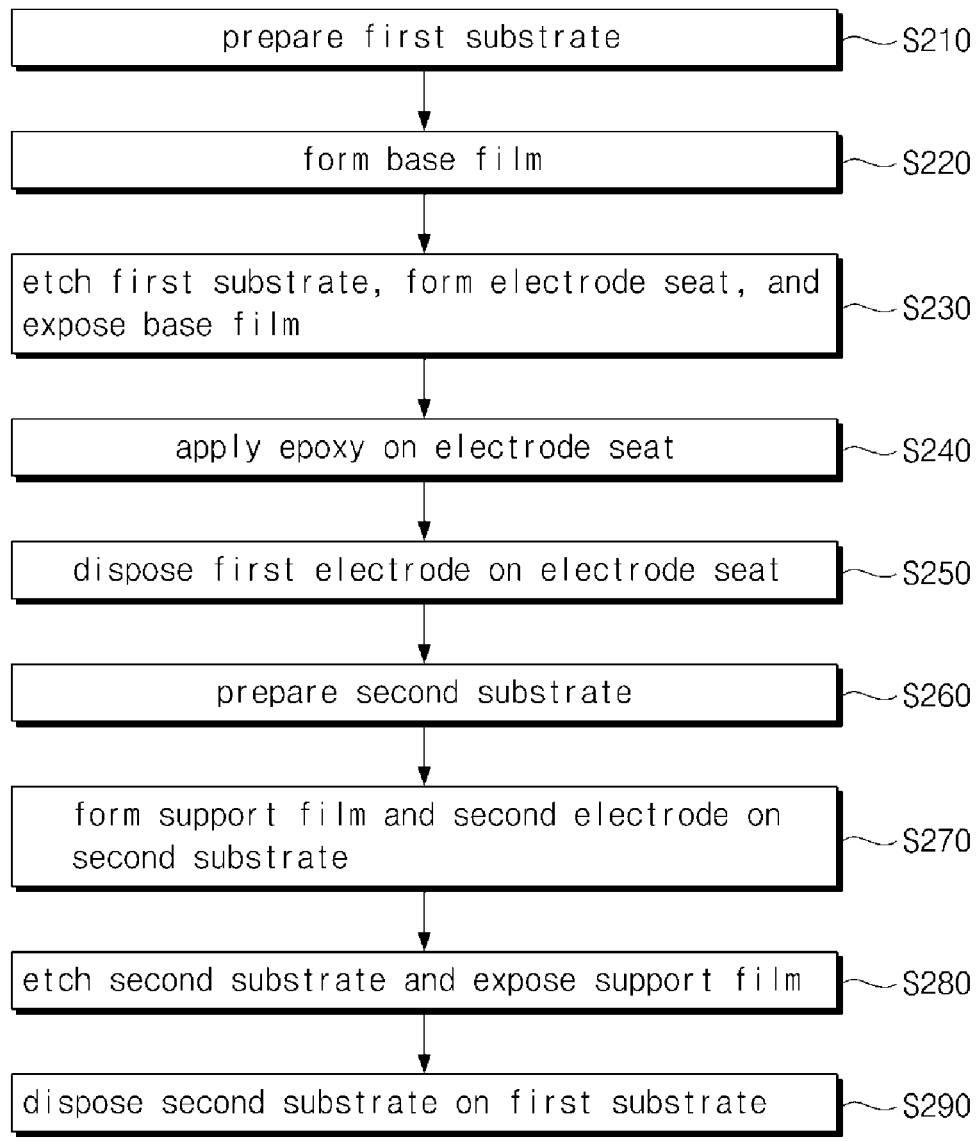

[FIG. 12]
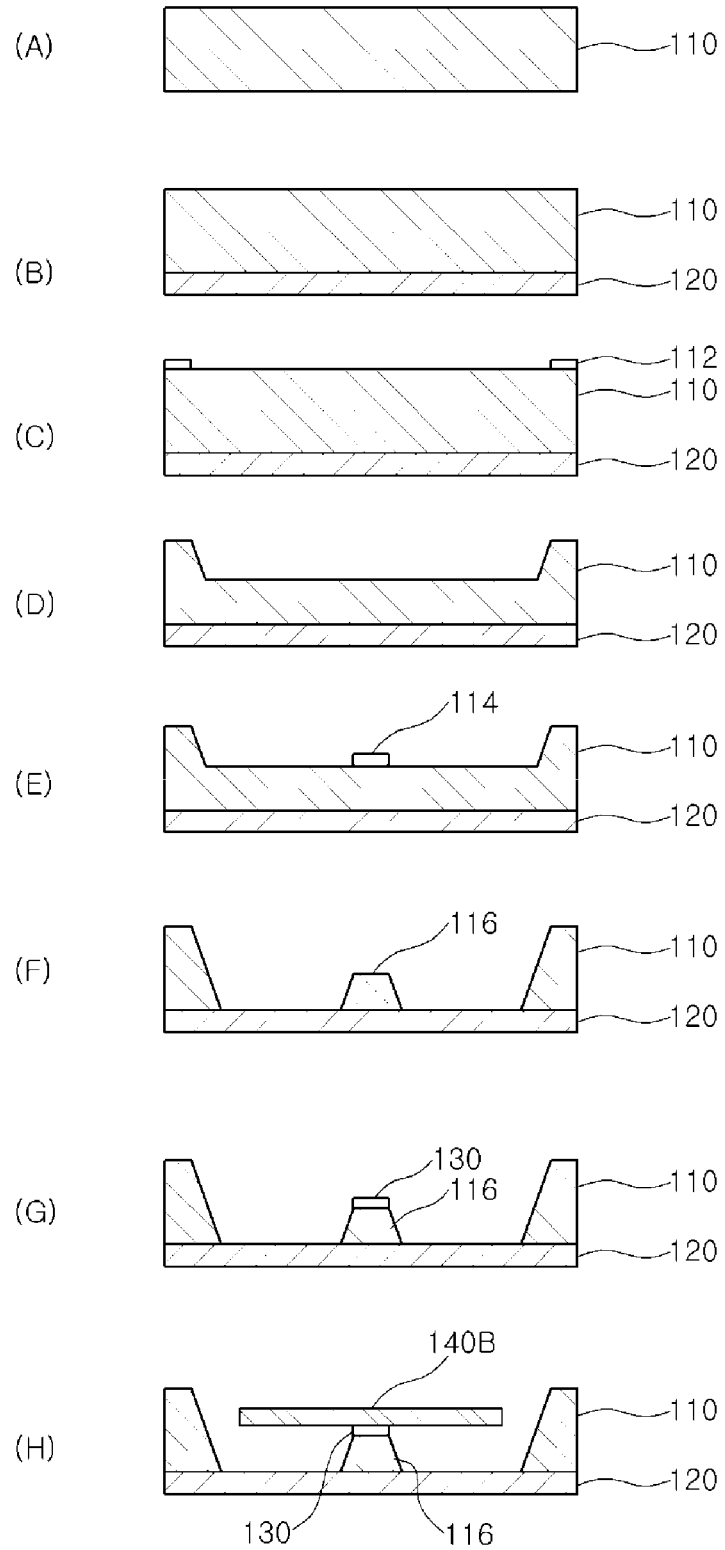

[FIG. 13]
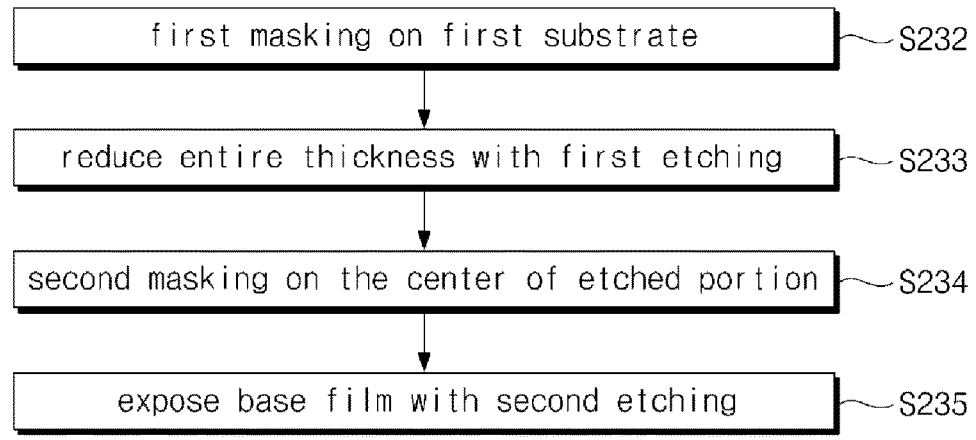
[FIG. 14]
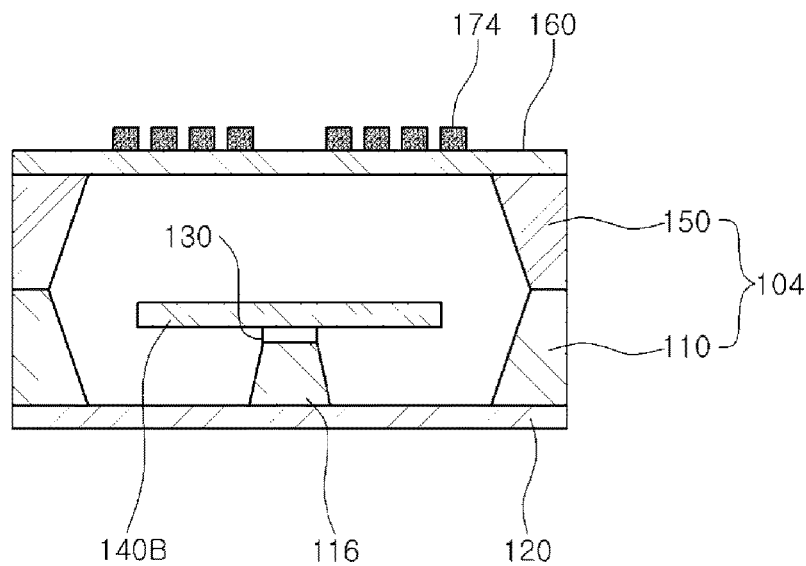

[FIG. 15]
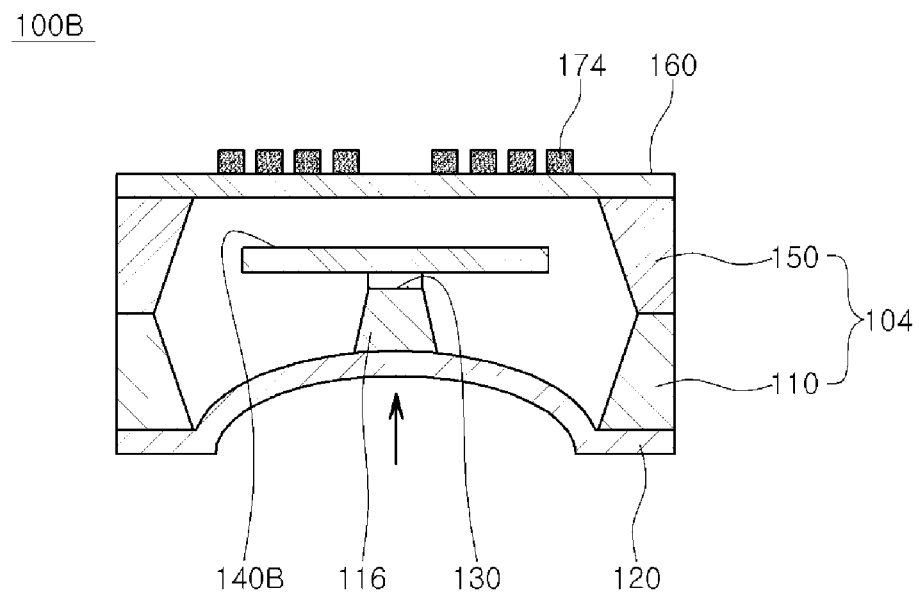

INTRAOCULAR PRESSURE SENSOR AND METHOD FOR MANUFACTURING SAME

CROSS REFERENCE TO PRIOR APPLICATIONS

This application is a National Stage Application of PCT International Patent Application No. PCT/KR2011/009009 filed on Nov. 24, 2011, under 35 U.S.C. §371, which claims priority to Korean Patent Application No. 10-2011-0102571 filed on Oct. 7, 2011, which are all hereby incorporated by reference in their entirety.

TECHNICAL FIELD

The present invention relates to an intraocular pressure sensor and a method of manufacturing the same, and more particularly to an intraocular pressure sensor that can improve the range and efficiency of measuring intraocular pressure, and a method of manufacturing the intraocular pressure sensor.

BACKGROUND ART

Intraocular pressure sensors measure the pressure of eyeballs of human body, that is, intraocular pressure.

Intraocular pressure sensors are used to accurately measure the intraocular pressure of a patient in order to diagnose and treat diseases associated with eyeballs. In particular, glaucoma is a disease due to damage to optic nerves that cannot stand against an increase in intraocular pressure and it is required to accurately measure the intraocular pressure of a patient in order to diagnose and treat glaucoma.

Therefore, there is a need of improving the range and efficiency of measuring intraocular pressure with a change in intraocular pressure.

DISCLOSURE

Technical Problem

The present invention has been made in an effort to solve the problems and an object of the present invention is to provide an intraocular pressure sensor that can improve the range and efficiency of measuring intraocular pressure of a patient, and a method of manufacturing the intraocular pressure sensor.

Another object of the present invention is to provide an intraocular pressure sensor that makes it easy to move its first electrode with a change in intraocular pressure by reducing the attachment area of the first electrode and a base film, and a method of manufacturing the intraocular pressure sensor.

Technical Solution

An aspect of the present invention provides a method of manufacturing an intraocular pressure sensor that is put into an eyeball of a patient and measures the intraocular pressure, which includes: preparing a first substrate; depositing a base film on the bottom of the first substrate; exposing the top of the base film by etching the first substrate; applying epoxy onto the center of the exposed base film; disposing the first electrode at the epoxy-applied portion on the base film; preparing a second substrate; depositing a support film onto the second substrate; forming a second electrode on the support film; exposing the bottom of the support film by etching the second substrate; and disposing the second substrate onto the first substrate.

Another aspect of the present invention provides a method of manufacturing an intraocular pressure sensor that is put into an eyeball of a patient and measures the intraocular pressure, which includes: preparing a first substrate; depositing a base film on the bottom of the first substrate; forming an electrode seat and exposing the top of the base film by etching the first substrate; applying epoxy onto the electrode seat; disposing the first electrode onto the electrode seat; preparing a second substrate; depositing a support film onto the second substrate; forming a second electrode on the support film; exposing the bottom of the support film by etching the second substrate; and disposing the second substrate onto the first substrate.

The areas of the first substrate and the second substrate may be the same.

The areas of the first substrate and the base film may be the same.

The areas of the second substrate and the support film may be the same.

The etching areas of the first substrate and the second substrate may be the same.

The portion of the first electrode which is attached to the base film may protrude.

An attachment hole may be formed at the portion of the first electrode which is attached to the base film.

The etching of the first substrate may include: first masking of masking the first substrate; first etching of etching the first substrate with a portion of the entire thickness of the first substrate remaining; second making of masking the center of the etched portion of the first substrate; and second etching of forming the electrode seat and exposing the base film by etching the first substrate.

The method may include disposing the second substrate on the first substrate with the etched portions are aligned.

Another aspect of the present invention provides an intraocular pressure sensor that is put in an eyeball of a patient and measures the intraocular pressure and that includes: a base film that is a reference surface for measuring intraocular pressure and applied with epoxy at the center portion; a body disposed along the edge on the base film; a first electrode formed in a plate shape, disposed on the base film, and having an attachment hole corresponding to the epoxy; a support film disposed on the top of the body; and a second electrode disposed on the support film.

Another aspect of the present invention provides an intraocular pressure sensor including: a base film that is a reference surface for measuring intraocular pressure; a body disposed along the edge on the base film; a base film disposed at the lower portion of the body; an electrode seat disposed on the base film; a first electrode formed in a plate shape and attached to the electrode seat by epoxy; a support film disposed on the top of the body; and a second electrode disposed on the support film.

Another aspect of the present invention provides an intraocular pressure sensor including: a base film that is a reference surface for measuring intraocular pressure; a body disposed along the edge on the base film; an electrode seat disposed on the base film; a first electrode formed in a plate shape and attached to the electrode seat by epoxy; a support film disposed on the top of the body; and a second electrode disposed on the support film.

An eddy current may be generated inside the body, and the magnitude of the eddy current may change with the distance between the first electrode and the second electrode.

The first electrode may contain ferrite, aluminum (Al), and copper (Cu).

The second electrode may contain aluminum (Al) and copper (Cu).

Advantageous Effects

According to the present invention, it is possible to improve the range and efficiency of measuring the intraocular pressure of a patient by minimizing the attachment surface of a base film and a first electrode at the lower portion in an intraocular pressure sensor.

DESCRIPTION OF DRAWINGS

FIG. 1 is a flowchart illustrating a method of manufacturing an intraocular pressure sensor according to a first embodiment of the present invention.

FIG. 2 is a view illustrating a process of processing a first substrate that is used in the method of manufacturing an intraocular pressure sensor according to the first embodiment of the present invention.

FIG. 3 is a view illustrating a process of processing a second substrate that is used in the method of manufacturing an intraocular pressure sensor according to the first embodiment of the present invention.

FIG. 4 is a perspective view illustrating an example of the second electrode illustrated in FIG. 3.

FIG. 5 is a cross-sectional view illustrating the configuration of an intraocular pressure sensor manufactured by the method of manufacturing an intraocular pressure sensor according to the first embodiment of the present invention.

FIG. 6 is a view illustrating the operation of the intraocular pressure sensor completed by the method of manufacturing an intraocular pressure sensor according to the first embodiment of the present invention.

FIG. 8 is a cross-sectional view illustrating the first electrode attached with a attachment hole formed in the method of manufacturing an intraocular pressure sensor according to the first embodiment of the present invention.

FIG. 9 is a view illustrating the configuration of an intraocular pressure sensor 100A using the first substrate illustrated in FIG. 8.

FIG. 10 is a view illustrating the operation of the intraocular pressure sensor illustrated in FIG. 9.

FIG. 11 is a flowchart illustrating a method of manufacturing an intraocular pressure sensor according to a second embodiment of the present invention.

FIG. 12 is a view illustrating a process of processing a first substrate that is used in the second embodiment of the present invention.

FIG. 13 is a flowchart a process of etching the first substrate in the method of manufacturing an intraocular pressure sensor according to the second embodiment of the present invention.

FIG. 14 is a cross-sectional view illustrating the configuration of the intraocular pressure sensor with the first electrode on an electrode seat.

FIG. 15 is a view illustrating the operation of the intraocular pressure sensor manufactured by the method of manufacturing an intraocular pressure sensor according to the second embodiment of the present invention.

BEST MODE

Hereinafter, exemplary embodiments of the present invention will be described with reference to accompanying drawings.

FIG. 1 is a flowchart illustrating a method of manufacturing an intraocular pressure sensor according to a first embodiment of the present invention.

The steps of the method of manufacturing an intraocular pressure sensor according to the first embodiment of the present invention are described with reference to the drawings.

FIG. 2 is a view illustrating a process of processing a first substrate that is used in the method of manufacturing an intraocular pressure sensor according to the first embodiment of the present invention.

Referring to (A) of FIG. 2, a step of preparing a first substrate (S110) is a step of preparing a first substrate 110 that makes the basic shape of an intraocular pressure sensor 100, together with a second substrate to be described below. The first substrate 110 is hard and has predetermined area and thickness.

Referring to (B) of FIG. 2, a step of forming a base film (S120) is a step of forming a base film 120 on the bottom of the first substrate 110, in which the base film 120 is formed on the bottom of the first substrate 110 by deposition.

The base film 120 is used as a reference surface for intraocular pressure measurement. It is preferable that the area of the base film 120 is the same as that of the first substrate 110.

The base film 120 is a flexible film and used for measuring intraocular pressure, so it is preferable that the base film 120 is made of a material harmless to the body or the eyeballs of a patient.

Referring to (C) and (D) of FIG. 2, a step of etching (S130) is to expose the base film 120 by etching the top of the first substrate 110 with the base film 120 attached.

The etching on the first substrate 110 may be performed as follows. That is, as illustrated in (C) of FIG. 2, the top of the first substrate 110 is partially covered, at the edge, by a mask 112. The mask 112 may be provided for 10~20% of the top of the first substrate 110, but it may be changed, if necessary for a user.

After the mask 112 is disposed, etching is performed such that the base film 120 is exposed through the etched portion, as illustrated in (D) of FIG. 2. The mask 112 is removed after the etching is finished.

A step of applying epoxy (S140) is performed, after the step of etching (S130) is performed.

Referring to (E) of FIG. 2, the step of applying epoxy (S140) is to apply epoxy 130 onto the base film 120 so that a first electrode 140 can be attached.

The epoxy is applied to the center portion of the base film 120 in the step of applying epoxy (S140). It is preferable to apply the epoxy 130 in as small area as possible within the range of attaching the first electrode 140.

The epoxy 130 may be a gel state or a liquid state to be easily applied.

The first electrode 140 is disposed after the step of applying epoxy (S140) is finished.

Referring to (F) of FIG. 2, a step of disposing a first electrode (S150) is to place the first electrode (140) onto the epoxy 130 on the base film 120.

The first electrode 140 generates an eddy current in the space to be defined by the first electrode 140 and a second electrode 174. It is preferable that the first electrode 140, which is a plate, is formed with as large area as possible to be vertically movable after disposed on the base film 120 through the etched portion of the first substrate 110.

The first electrode 140 may contain ferrite, aluminum (Al), and copper (Cu).

The first electrode 140 is attached to the base film 120 by the epoxy on the base film 120. An attachment projection 141 with a rectangular cross-section is formed on the attachment surface of the first electrode 140 which is attached to the base film 120.

When the first electrode 140 is disposed, after the attachment portion 141 of the first electrode 140 is disposed on the epoxy 130 on the base film 120 and the epoxy is hardened, the first film 140 is fixed.

Since the attachment area of the first electrode 140 and the base film 120 are a portion of the entire area of the first electrode 140, the first electrode 140 can more easily move when the base film 120 moves up/down with a change in intraocular pressure.

FIG. 3 is a view illustrating a process of processing a second substrate that is used in the method of manufacturing an intraocular pressure sensor according to the first embodiment of the present invention.

Referring to (A) of FIG. 3, a step of preparing a second substrate (S160) is a step of preparing a second substrate 150 the makes the entire shape of the intraocular pressure sensor 100 together with the first substrate 110.

It is preferable that the area and thickness of the second substrate 150 are the same as those of the first substrate 110 and the material of the second substrate 150 is the same as that of the first substrate 110.

Referring to (B) of FIG. 3, in a step of forming a support film and a second electrode on the second substrate (S170), a support film 160 is formed on the top of a second substrate 150 by deposition. The support film 160 supports the second electrode to be described below, when the intraocular pressure sensor is used.

Referring to (C), (D), and (E) of FIG. 3, in the step of forming a support film and a second electrode (S170), a second electrode 174 generating an eddy current in the intraocular pressure sensor is formed to correspond to the first electrode 140.

As illustrated in (C) of FIG. 3, a metal layer 170 is deposited first onto the support film 160. The metal layer 170 contains copper (Cu), or aluminum (Al), or a copper-aluminum alloy.

Referring to (D) of FIG. 3, a mask 172 corresponding to the shape of the second electrode 174 is disposed on the metal layer 170 and the metal layer 170 is etched, thereby forming the second electrode 174, as illustrated in (E) of FIG. 3.

FIG. 4 is a perspective view illustrating an example of the second electrode illustrated in FIG. 3.

The shape of the second electrode 174 is not limited to that illustrated in the figure and may be changed in various ways, if necessary for a user.

The second electrode 174 generates an eddy current in the space defined by the first electrode 140 and the second electrode 174 in accordance with the gap therebetween.

Refer to FIG. 3 again.

Referring to (F) and (G) of FIG. 3, a step of etching the second substrate (S180) is to expose the bottom of the support film 160 by etching the bottom of the second substrate 150.

The etching on the second substrate 150 may be performed as follows. That is, as illustrated in (F) of FIG. 3, a mask 152 is partially disposed on the edge of the bottom of the second substrate 150. The mask 152 may be provided for 10~20% of the bottom of the second substrate 150, but it may be changed, if necessary for a user.

After the mask 152 is disposed, etching is performed such that the support film 160 is exposed through the etched portion, as illustrated in (G) of FIG. 2. The mask 152 is removed after the etching is finished.

It is preferable that the etching area of the second substrate 150 is the same as that of the first substrate 110.

After the second substrate 150 is etched, the intraocular pressure sensor 100 is completed by disposing the second substrate 150 onto the first substrate 110 with the first electrode 140 attached on the base film 120.

FIG. 5 is a cross-sectional view illustrating the configuration of an intraocular pressure sensor manufactured by the method of manufacturing an intraocular pressure sensor according to the first embodiment of the present invention.

Referring to FIG. 5, it can be seen that the portions of the first and second substrates 110 and 150 which remain after the first and second substrates 110 and 150 are etched (S130 and S180) are vertically connected in contact with each other, thereby forming a body 104 with a space therein where an eddy current is generated.

It can be seen that the base film 120 and the support film 160 are on the top and the bottom of the body 104.

Since the first electrode 140 is on the base film 120 and the second electrode 174 is on the support film 160, an eddy current according to the gap can be generated in the space between the first electrode 140 and the second electrode 174.

This configuration can be used in the same way for the intraocular pressure sensor to be described below.

The operation of the present invention with the configuration described above is described hereafter.

The intraocular pressure sensor 100 illustrated in FIG. 5 is positioned in an eyeball (not illustrated).

Under normal intraocular pressure, the gap between the first electrode 140 and the second electrode 174 is maintained at the initial level, as illustrated in FIG. 5.

FIG. 6 is a view illustrating the operation of the intraocular pressure sensor completed by the method of manufacturing an intraocular pressures sensor according to the first embodiment of the present invention, in which the relationship between the first electrode 140 and the second electrode 174 with intraocular pressure increased at a predetermined level is illustrated.

As illustrated in the figure, the center portion of the base film 120 is pushed up by an increase in intraocular pressure and the gap between the first electrode 140 and the second electrode 174 is reduced.

Since the eddy current between the first electrode 140 and the second electrode 174 increases, it is possible to measure the increase in intraocular pressure by sending the eddy current.

Since the attachment area of the first electrode 140 and the base film 120 are a portion of the entire area of the first electrode 140, the first electrode 140 can more easily move when the base film 120 moves up/down with a change in intraocular pressure.

FIG. 7 is a view illustrating eddy current generation in the intraocular pressure sensor completed by the method of manufacturing an intraocular pressure sensor according to the first embodiment of the present invention.

That is, as illustrated in FIG. 7, an eddy current is generated between the first electrode 140 and the second electrode 174. Since the eddy current acts to reduce the inductance of an inductor, if the first electrode 140 and the second electrode 174 come closer to each other due to an increase in pressure outside the intraocular pressure sensor, the magnitude of the eddy current inside the body 104 increases and the inductance of an inductor decreases accordingly.

When the distance between the first electrode 140 and the second electrode 174 is changed by the pressure outside the intraocular pressure sensor, the parasitic component of the inductor by the second electrode 174 changes and the change of the parasitic component causes the impedance of the intraocular pressure sensor to change. It is possible to know the pressure in an eyeball at the outside by detecting the change of the impedance of the intraocular pressure sensor at the outside.

That is, since the amount of the eddy current changes with the distance between electrodes, it is possible to measure intraocular pressure by measuring a change in eddy current according to a change in distance between the first electrode 140 and the second electrode 174. The change in eddy current according to the distance between electrodes is separately measured.

When the first electrode is attached in the process of manufacturing the intraocular pressure sensor, the epoxy applied on the base film 120 may be pushed by the pressure for attaching the electrode, such that the epoxy-applied portion may expand unlike the user's intention.

FIG. 8 is a cross-sectional view illustrating the first electrode attached with a bonding hole formed in the method of manufacturing an intraocular pressure sensor according to the first embodiment of the present invention.

FIG. 9 is a view illustrating the configuration of an intraocular pressure sensor 100A using the first substrate illustrated in FIG. 8.

Referring to FIGS. 8 and 9, an attachment hole 142 is formed through the center of a first electrode 140A. It is preferable that the area of the attachment hole 142 is smaller than the epoxy-applied area.

When the first electrode 140A with the attachment hole 142 is disposed on a base film 120 with epoxy applied, the epoxy 140 bonds the first electrode 140A to the base film 120. The epoxy flows into the attachment hole 142 due to the pressure for attaching the first electrode 140A and can prevent the attachment area of the base film 120 and the first electrode 140A from expanding over a predetermined level.

FIG. 10 is a view illustrating the operation of the intraocular pressure sensor illustrated in FIG. 9.

The intraocular pressure sensor 100A illustrated in FIG. 10 has the same configuration and operation as those of the intraocular pressure sensor 100 illustrated in FIGS. 5 and 6, except that the attachment hole 142 is formed through the first electrode 140A, so the detailed description is not provided.

FIG. 11 is a flowchart illustrating a method of manufacturing an intraocular pressure sensor according to a second embodiment of the present invention and FIG. 12 is a view illustrating a process of processing a first substrate that is used in the second embodiment of the present invention.

The method of manufacturing an intraocular pressure sensor according to the second embodiment of the present invention is described with reference to the figures.

The same configuration as that of the previous embodiment is not described in detail and only the difference is described.

In this embodiment, an electrode seat 116 is formed on a base film 120 to minimize the attachment area for fixing a first electrode 140B.

The electrode seat 116 is formed in a step of etching the first substrate (S230).

To this end, the step of etching the first substrate (S230) is performed as follows.

FIG. 13 is a flowchart the step of etching the first substrate (S230) in the method of manufacturing an intraocular pressure sensor according to the second embodiment of the present invention.

Referring to FIG. 13, the step of etching the first substrate includes first masking (S232), first etching (S233), second masking (S234), and second etching (S235).

The first masking (S232) is a step of disposing a first mask 112 onto the surface to be etched of the first substrate 110. The first mask 112, as illustrated in (C) of FIG. 12, is disposed to partially cover the edge of the top of the first substrate 110. The first mask 112 may be disposed to cover 10~20% of the top of the first substrate 110, but it may be changed, if necessary for a user.

The first etching (S233) is performed, as illustrated in (D) of FIG. 12, after the first mask 112 is disposed. The first etching S233 is continued until the etched portion of the first substrate 110 decreases about half in thickness.

When the etched portion of the first substrate 110 decreases about half in thickness, the first etching (S233) is ended. Although the first etching (S233) is continued until the etched portion of the first substrate 110 decreases half in thickness in this embodiment, it is limited to when the height of the electrode seat 116 is a half of the height of the first substrate 110 and the degree of the first etching (S233) may change in accordance with the height of the electrode seat 116.

Thereafter, a second mask 114 is disposed in a predetermined area on the center of the etched surface, as illustrated in (E) of FIG. 12. The area of the second mask 114 is determined at a level correspond to the top area of the electrode seat 116 which is described below.

The second etching (S235) for etching the top of the first substrate 110 is performed, as illustrated in (F) of FIG. 12, after the second mask 114 is disposed. The second etching (S235) is continued until the base film 120 is exposed through the etched portion formed in the first etching (S233). The electrode seat 116 having predetermined height and diameter is formed without the portion where the second mask 114 is positioned removed. The second mask 114 is removed, when the second etching (S235) is finished.

As illustrated in (G) of FIG. 12, the epoxy applying (S240) is to apply epoxy onto the top of the electrode seat 116 formed in the second etching (S235).

Thereafter, the first electrode 140B is disposed onto the electrode seat 116 (S250).

FIG. 14 is a cross-sectional view illustrating the configuration of an intraocular pressure sensor 100B with the first electrode 140B on the electrode seat 116.

Although the first electrode 140B is formed in a flat plate, an attachment hole may be formed and an electrode seat may be formed, as in the previous embodiment.

After the first substrate 110 and the second substrate 150 are etched, as illustrated in FIG. 14, the first substrate 110 and the second substrate 150 are aligned and combined, thereby completing the intraocular pressure sensor 100B.

FIG. 15 is a view illustrating the operation of the intraocular pressure sensor manufactured by the method of manufacturing an intraocular pressure sensor according to the second embodiment of the present invention.

The operation of the intraocular pressure sensor manufactured by the manufacturing method of this embodiment is the same as that of the intraocular pressure sensor manufactured by the manufacturing method according to the previous embodiment and the detailed description is not provided.

Although the present invention has been described with reference to the embodiments illustrated in the drawings, those are only examples and may be changed and modified into other equivalent embodiments from the present invention by those skilled in the art. Therefore, the technical protective region of the present invention should be determined by the scope described in claims.

The invention claimed is:

1. A method of manufacturing an intraocular pressure sensor that is put into an eyeball of a patient and measures the intraocular pressure, the method comprising:
preparing a first substrate;
depositing a base film on the bottom of the first substrate;
exposing the top of the base film by etching the first substrate;
applying epoxy onto the center of the exposed base film;
disposing a first electrode at the epoxy-applied portion on the base film;
preparing a second substrate;
depositing a support film onto the second substrate;
forming a second electrode on the support film;
exposing the bottom of the support film by etching the second substrate; and
disposing the second substrate onto the first substrate so that the second electrode protruding outside of an internal space interposed between the first substrate and the second substrate.

2. The method of claim 1, wherein areas of the first substrate and the second substrate are the same.

3. The method of claim 2, wherein the areas of the first substrate and the base film are the same.

4. The method of claim 2, wherein the areas of the second substrate and the support film are the same.

5. The method of claim 1, wherein the etching areas of the first substrate and the second substrate are the same.

6. The method of claim 1, wherein a portion of the first electrode which is attached to the base film protrudes.

7. The method of claim 1, wherein an attachment hole is formed at the portion of the first electrode which is attached to the base film.

8. The method of claim 1, comprising disposing the second substrate on the first substrate with the etched portions are aligned.

9. A method of manufacturing an intraocular pressure sensor that is put into an eyeball of a patient and measures the intraocular pressure, the method comprising:
preparing a first substrate;
depositing a base film on the bottom of the first substrate;
forming an electrode seat and exposing the top of the base film by etching the first substrate;
applying epoxy onto the electrode seat;
disposing a first electrode onto the electrode seat;
preparing a second substrate;
depositing a support film onto the second substrate;
forming a second electrode on the support film;
exposing the bottom of the support film by etching the second substrate; and
disposing the second substrate onto the first substrate so that the second electrode protruding outside of an internal space interposed between the first substrate and the second substrate.

10. The method of claim 9, wherein the etching of the first substrate includes:
first masking of masking the first substrate;
first etching of etching the first substrate with a portion of the entire thickness of the first substrate remaining;
second making of masking the center of the etched portion of the first substrate; and
second etching of forming the electrode seat and exposing the base film by etching the first substrate.

11. The method of claim 9, wherein areas of the first substrate and the second substrate are the same.

12. The method of claim 9, comprising disposing the second substrate on the first substrate with the etched portions are aligned.

* * * * *